(12) United States Patent
Wissner et al.

(10) Patent No.: US 7,399,865 B2
(45) Date of Patent: Jul. 15, 2008

(54) PROTEIN TYROSINE KINASE ENZYME INHIBITORS

(75) Inventors: Allan Wissner, Ardsley, NY (US); Sridhar Krishna Rabindran, Chestnut Ridge, NY (US); Hwei-Ru Tsou, New City, NY (US)

(73) Assignee: Wyeth, Madison, NJ (US)

( * ) Notice: Subject to any disclaimer, the term of this patent is extended or adjusted under 35 U.S.C. 154(b) by 475 days.

(21) Appl. No.: 10/939,007

(22) Filed: Sep. 10, 2004

(65) Prior Publication Data

US 2005/0059678 A1   Mar. 17, 2005

Related U.S. Application Data

(60) Provisional application No. 60/560,724, filed on Sep. 15, 2003.

(51) Int. Cl.
C07D 215/38 (2006.01)
(52) U.S. Cl. .................. 546/160; 546/153; 546/152
(58) Field of Classification Search ............... 514/313, 514/312, 311; 546/160, 153, 152
See application file for complete search history.

(56) References Cited

U.S. PATENT DOCUMENTS

| 6,288,082 B1 * | 9/2001 | Wissner et al. ............ 514/313 |
| 6,288,802 B1 | 9/2001 | Hoshina et al. |
| 6,821,988 B2 * | 11/2004 | Wissner et al. ............ 514/313 |

FOREIGN PATENT DOCUMENTS

| WO | WO 98/43960 | 10/1998 |
| WO | WO 2000/018761 | * 4/2000 |
| WO | WO 03/050090 A1 | 6/2003 |
| WO | WO 2004/096224 A2 | 11/2004 |

OTHER PUBLICATIONS

Kin, CA 136:308014 abstract only of Oncology Reports, VOl 9(1), pp. 3-9, 2002.*
Hung, CA 132:135559, abstract only of seminars in Oncology, vol. 25(4, Suppl. 12), pp. 51-59, 1999.*
Plosker, Drugs, vol. 66(4), pp. 449-475, 2006.*
UPESLACIS, Janis, Oct. 16, 2002, meeting at McGill University, Canada, Evolution of Kinase Inhibitors at Wyeth.
Rabindran, S. K., et al.; Antitumor Activity of HKI-272, an Orally Active, Irreversible Inhibitor of the HER-2 Tyrosine Kinase; Cancer Research 64:3958-3965; Jun. 1, 2004.

* cited by examiner

*Primary Examiner*—D. Margaret Seaman
(74) *Attorney, Agent, or Firm*—Stephen E. Johnson

(57) ABSTRACT

This invention provides compounds of formula 1, having the structure

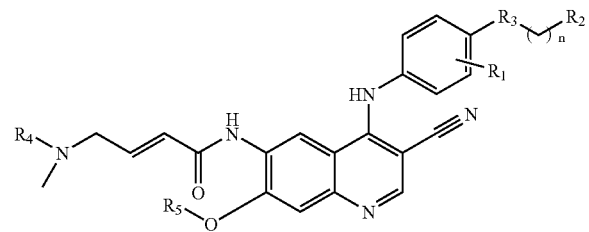

wherein $R_1$, $R_2$, $R_3$, $R_4$, and $R_5$ are described within the specification.

10 Claims, No Drawings

PROTEIN TYROSINE KINASE ENZYME INHIBITORS

This application claims priority from copending provisional application Ser. No. 60/560,724, filed Sep. 15, 2003, converted from nonprovisional application Ser. No. 10/662,273, filed Sep. 15, 2003, the entire disclosure of which is hereby incorporated by reference.

BACKGROUND OF THE INVENTION

This invention relates to certain substituted 3-cyano quinoline compounds as well as the pharmaceutically acceptable salts thereof. The compounds of the present invention inhibit the HER-2 and epidermal growth factor receptor (EGFR) enzyme thereby inhibiting the abnormal growth of certain cell types. The compounds of this invention are anti-cancer agents and are useful for the treatment of cancer in mammals. This invention also relates to the use of 3-cyano quinolines in the treatment of cancer and the pharmaceutical preparations containing them.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or over expression, these receptors can become deregulated, the result of which is uncontrolled cell proliferation which can lead to tumor growth and ultimately to the disease known as cancer [Walks, A. F., *Adv. Cancer Res.*, 60, 43 (1993) and Parsons, J. T.; Parsons, S. J., *Important Advances in Oncology*, DeVita, V. T. Ed., J. B. Lippincott Co., Phila, 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER-2) oncogene. Since the phosphorylation event is a necessary signal for cell division to occur and since over expressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, over expression of the receptor kinase product of the erbB-2 oncogene has been associated with human breast and ovarian cancers [Slamon, D. J., et. al., *Science*, 244, 707 (1989) and *Science*, 235, 1146 (1987)]. Deregulation of EGF-R kinase has been associated with epidermoid tumors [Reiss, M., et al., *Cancer Res.*, 51, 6254 (1991)], breast tumors [Macias, A., et. al., *Anticancer Res.*, 7, 459 (1987)], and tumors involving other major organs [Gullick, W. J., *Brit. Med. Bull.*, 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke. T. R., *Drugs Future*, 17, 119 (1992) and Chang, C. J.; Geahlen, R. L., *J. Nat. Prod.*, 55, 1529 (1992)]. The compounds of this invention inhibit the kinase activity of EGF-R and are therefore useful for treating certain disease states, such as cancer, that result, at least in part, from deregulation of this receptor.

The HER-2 gene (c-erbB-2, neu) encodes a 185 kDa transmembrane tyrosine kinase receptor that has partial homology with other members of the epidermal growth factor receptor family [Shih, C., Padhy, L. C., Murray, M., et al. Transforming genes of carcinomas and neuroblastomas introduced into mouse fibroblasts, *Nature*, 290, 261-264 (1981)]. It is now known that normal human cells express a small constitutive amount of HER-2 protein on the plasma membrane. The activation of the HER-2 oncogene is believed to follow the binding of a yet unidentified growth factor ligand to the HER-2 receptor complex, which leads to heterodimerization, triggering a cascade of growth signals that culminates in gene activation. More specifically, the epidermal growth factor family can be subdivided into four groups based on their receptor-binding specificities (HER-1, HER-2, HER-3, and HER-4). HER-2 is the preferred heterodimerization partner of all other HER receptors. Over expression of HER-2 has been demonstrated to lead to increased tumorigenicity, tumor invasiveness, increased metastatic potential, and altered sensitivity to hormonal and chemotherapeutic agents in transfection studies in cellular and animal models [Pegram, M. D., Finn, R. S., Arzoo, K., et al. The effect of HER-2/neu over expression on chemotherapeutic drug sensitivity in human breast and ovarian cells *Oncogene*, 15, 537-547 (1997)].

HER-2 protein over expression has been reported to occur in approximately 30% of invasive human breast cancers, with HER-2 gene amplification detected in 95% or more of the specimens found to over express HER-2 protein, [Gebhardt, F., Zänker, K., Brandt, B. Differential expression of alternatively spliced c-erbB-2 mRNA in primary tumors, lymph node metastases, and bone marrow micro metastases from breast cancer patients *Biochem. Biophys. Res. Commun.*, 247, 319-323 (1998)].

U.S. Pat. No. 6,288,082 issued Sep. 11, 2001 (the '082 patent) discloses substituted 3-cyano quinoline compounds that inhibit epidermal growth factor receptor (EGFR). The compounds of this application are distinguished from those of the '082 patent in their ability to act as potent HER-2 inhibitors.

BRIEF SUMMARY OF THE INVENTION

This invention provides a compound of formula 1:

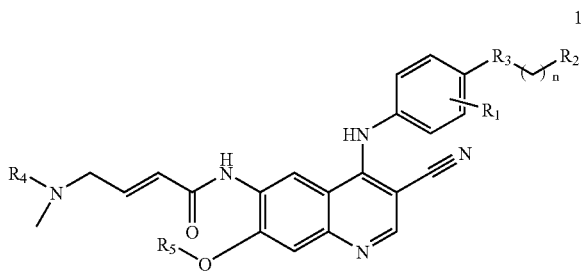

wherein:
$R_1$ is halogen;
$R_2$ is a pyridinyl, thiophene, pyrimidine, thiazole, or phenyl optionally substituted with up to three substituents;
$R_3$ is —O— or —S—;
$R_4$ is methyl or $CH_2CH_2OCH_3$;
$R_5$ is ethyl or methyl; and
n is 0 or 1.

In one embodiment the compounds of this invention include:

(E)-N-{4-[4-(benzyloxy)-3-chloroanilino]-3-cyano-7-ethoxy-6-quinolinyl}-4-(dimethylamino)-2-butenamide;

(E)-N-{4-[3-chloro-4-(2-pyridinylmethoxy)anilino]-3-cyano-7-ethoxy-6-quinolinyl}-4-(dimethylamino)-2-butenamide;

(E)-N-(4-{3-chloro-4-[(3-fluorobenzyl)oxy]anilino}-3-cyano-7-ethoxy-6-quinolinyl)-4 -(dimethylamino)-2-butenamide;

(2E)-N-(4-{[3-chloro-4-(1,3-thiazol-2-ylsulfanyl)phenyl]amino}-3-cyano-7-methoxy -6-quinolinyl)-4-(dimethylamino)-2-butenamide;

(E)-N-(4-{3-chloro-4-[(4,6-di-methyl-2-pyrimidinyl)sulfanyl]anilino}-3-cyano-7-ethoxy -6-quinolinyl)-4-(dimethylamino)-2-butenamide;

(E)-N-{4-[3-chloro-4-(1,3-thiazol-2-ylsulfanyl)anilino]-3-cyano-7-methoxy-6-quinolinyl}-4-[(2-methoxyethyl)(methyl)amino]-2-butenamide;

The following experimental details are set forth to aid in an understanding of the invention, and are not intended, and should not be construed, to limit in any way the invention set forth in the claims that follow thereafter.

DETAILED DESCRIPTION OF THE INVENTION

The compounds of this invention are certain substituted 3-cyano quinolines. Throughout this patent application, the quinoline ring system will be numbered as indicated in the formula below; the numbering for the quinazoline ring system is also shown:

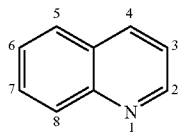 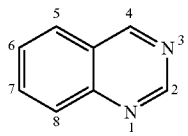

The pharmaceutically acceptable salts of the compounds of this invention are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

For purposes of this invention "halogen" is F, Cl, Br, or I.

Where a group is referred to as "substituted", preferred substituents are selected from alkyl of up to six carbon atoms, alkoxy, of up to six carbon atoms and halogen. A particularly preferred substituent is methyl.

The compounds of this invention may contain one or more asymmetric carbons atoms; in such cases, the compounds of this invention include the individual diasteromers, the racemates, and the individual R and S entantiomers thereof. Some of the compounds of this invention may contain one or more double bonds; in such cases, the compounds of this invention include each of the possible configurational isomers as well as mixtures of these isomers.

For purposes of this invention a "neoplasm" is defined as cells selected from the breast, kidney, bladder, mouth, larynx, esophagus, stomach, colon, ovary, pancreas, brain, prostrate and lung having a morphology not found in the majority of the cells of a mammal.

In one embodiment, the present invention provides for a method of inhibiting the neoplasm. The method comprises contacting a cell with an amount of a compound effective to decrease or prevent HER-2 function. The cell may be a mammalian cell and more specifically a human cell. The cell may also be a bacterial cell such as for example E. Coli. The cell may include but is not limited to, a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell, a ganglion cell or a stem cell. The cell may be a normal cell, an activated cell, a neoplastic cell, a diseased cell, or an infected cell.

In another embodiment, the present invention provides a method for the treatment or prevention of a neoplasm in a mammal. The present invention accordingly provides to a mammal, a pharmaceutical composition that comprises a compound of this invention in combination or association with a pharmaceutically acceptable carrier. The compound of this invention may be administered alone or in combination with other therapeutically effective compounds or therapies for the treatment or prevention of the neoplasm.

The compounds may be provided orally, by intralesional, intraperitoneal, intramuscular or intravenous injection; infusion; liposome-mediated delivery; topical, nasal, anal, vaginal, sublingual, urethreal, transdermal, intrathecal, ocular or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 300 mg of a compound of the invention and preferably from 2 to 100 mg. Still further preferred unit dosage forms contain 5 to 50 mg of a compound of the present invention. The compounds of the present invention can be administered orally at a dose range of about 0.01 to 100 mg/kg or preferably at a dose range of 0.1 to 10 mg/kg. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers useful in treatment or prevention of neoplasm. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroblasts. Such compositions will influence the physical state, solubility, stability, rate of in vivo release, and rate of in vivo clearance of the compound or composition. The choice of compositions will depend on the physical and chemical properties of the compound capable of treating or preventing a neoplasm.

The compound of the present invention may be delivered locally via a capsule that allows a sustained release of the compound over a period of time. Controlled or sustained release compositions include formulation in lipophilic depots (for example, fatty acids, waxes, oils).

The present invention further provides a compound of the invention for use as an active therapeutic substance for preventing neoplasm.

The present invention further provides a method of treating neoplasm in humans, which comprises administering to the infected individual an effective amount of a compound or a pharmaceutical composition of the invention.

The compounds of this invention can be prepared as outlined in Flowsheet 1 wherein $R_1$, $R_2$, and $R_3$ are as described above. The amino group of compound 1 can be protected as an amide group by acetylation using acetic anhydride in a solvent such as acetic acid. The hydroxyl group of 2 can be alkylated with an alkyl bromide, iodide, tosylate, or mesylate using potassium carbonate in a refluxing solvent such as acetone. The nitro group of 3 can be reduced using catalytic hydrogenation to give the substituted aniline 4. Heating of 4 with reagent 5 with or without a solvent gives the intermediate 6. Refluxing 6 in a high boiling solvent such as Dowtherm results in cyclization to the hydroxy quinoline 7. This can be chlorinated by heating in phosphorous oxychloride to give the chloro derivative 8. Condensation of 8 with an aniline of formula 9 in a refluxing solvent such as ethanol in the presence of a catalytic amount of acid yields the intermediate 10. The acetate group of 10 can be removed by hydrolysis using acidic or basic conditions followed by neutraliztion to give 11. The intermediate 11 can be acylated with an amino acid chloride 12 (as the hydrochloride salt) to give the compounds of this invention of formula 13. Methods used to prepare the compounds in U.S. Pat. No. 6,288,082, WO-9633978 and WO-9633980 can also be used to prepare the compounds of this invention and are hereby incorporated by reference.

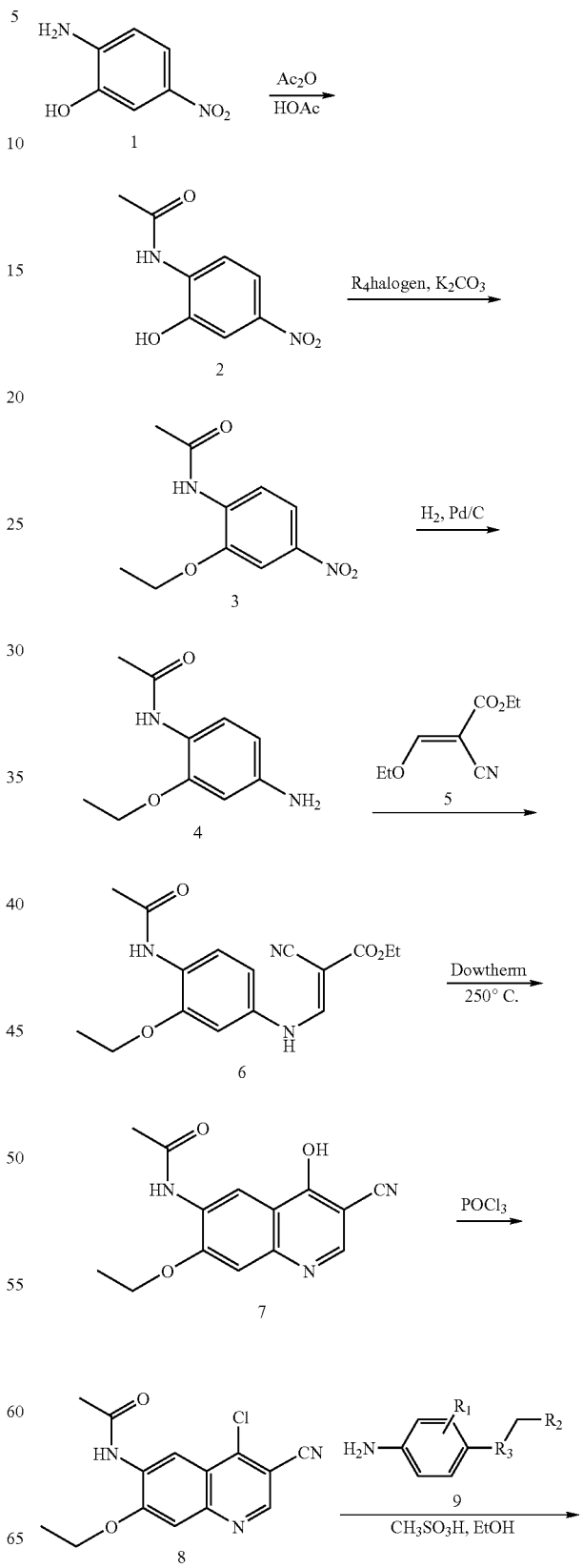

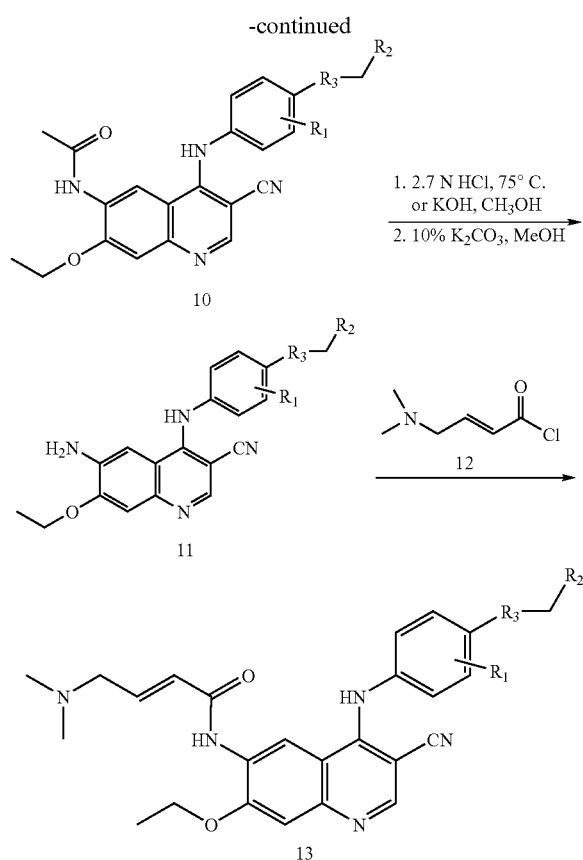

In addition to the method described herein above, there a number of patent applications that describe methods that are useful for the preparation of the compounds of this invention. Although these methods describe the preparation of certain quinazolines, they are also applicable to the preparation of correspondingly substituted 3-cyanoquinolines and are hereby incorporated by reference. The chemical procedures described in the application WO-9633980 can be used to prepare the 3-cyanoquinoline intermediates used in this invention wherein the substitution at position 6 is an aminoalkylalkoxy group. The chemical procedures described in the application WO-9633978 can be used to prepare the 3-cyanoquinoline intermediates used in this invention wherein the substitution at position 6 is an aminoalkylamino group.

EXAMPLE 1

(E)-N-{4-[4-(benzyloxy)-3-chloroanilino]-3-cyano-7-ethoxy-6-quinolinyl}-4-(dimethylamino)-2-butenamide A 1.74 ml (2.54 g, 0.02 moles) portion of oxalyl chloride was added to 3.31 grams (0.02 moles) of (E)-4-(dimethylamino)-2-butenoic acid hydrochloride in 75 ml of acetonitrile. To this was added a small drop of dimethylformamide. The reaction was heated and stirred in an oil bath at 63° for 20 minutes, giving an orange solution. This solution as concentrated in vacuo without the application of heat to about half its original volume. This solution was cooled in an ice bath and a solution of 4.45 g (0.01 moles) of the 6-amino-4-[4-(benzyloxy)-3-chloroanilino]-7-ethoxy-3-quinolinecarbonitrile in 50 ml of N-methylpyrrolidone was added in a stream. The reaction was cooled and stirred for 2 hours. The reaction was poured onto 100 ml of saturated aqueous sodium bicarbonate in ice. On standing the resulting gum solidified and the solid was filtered. This solid was chromatographed on silica gel. The column was washed with 3 liters of 1:19 methanol-ethyl acetate, then the product was eluted with 3 liters of 1:5:94 triethylamine-methanol-ethyl acetate. Concentration of the eluate gave a solid, which was filtered to give 2.96 grams of the title compound. From the filtrate was obtained an additional 1.0 grams of product. Total: 3.96 g.

EXAMPLE 2

(E)-N-{4-[3-chloro-4-(2-pyridinylmethoxy)anilino]-3-cyano-7-ethoxy-6-quinolinyl}-4-(dimethylamino)-2-butenamide A solution of (E)-4-(dimethylamino)-2-butenoic acid hydrochloride in 1.2 L of tetrahydrofuran (THF) and a catalytic amount of dimethylformide (DMF) (1.2 ml) was cooled to 0-5° C. Oxalyl chloride (0.95 eq) was added dropwise and the mixture was warmed to 25-30° C. and stirred for 2 hours. The orange suspension was checked for complete consumption of oxalyl chloride by HPLC then cooled to 0-5° C. A solution of 111 g of 4-[4-(2-pyridylmethoxy)-3-chloro]amino-6-amino-3-cyano-7-ethoxyquinoline in 1.47 L of 1-methyl-2-pyrrolidinone was added dropwise and the mixture was stirred until ≦1.0% of the starting aniline remained (3-16 hours). The reaction was quenched with water and the mixture was warmed to 40° C. Aqueous sodium hydroxide was added to bring the pH to 10-11. The resulting precipitates were filtered hot and washed with water. The wet solids were heated to reflux (70-75° C.) in acetonitrile:THF (1.5:1) and the solution cooled over 3 hours to room temperature. The product was filtered and washed with acetonitrile:THF. The product was dried (50° C., 10 mm Hg, 24 hours) to give 80-85% yield. Melting point of maleate salt 178-183° C.

EXAMPLE 3

(E)-N-(4-{3-chloro-4-[3-fluorobenzyl)oxy]anilino}-3-cyano-7-ethoxy-6-quinolinyl)-4-(dimethylamino)-2-butenamide A solution of 108 g (E)-4-(dimethylamino)-2-butenoic acid hydrochloride in 1.1 L of tetrahydrofuran (THF) and a catalytic amount of dimethylformide (DMF) (1.2 ml) was cooled to 0-5° C. Oxalyl chloride (0.95 eq) was added dropwise and the mixture was warmed to 25-30° C. and stirred for 2 hours. The orange suspension was checked for complete consumption of oxalyl chloride by HPLC then cooled to 0-5° C. A solution of 150 g of 6-amino-4-[3-chloro-4-(3-fluorobenzyloxy)]anilino-3-cyano-7-ethoxy quinoline in 1.5 L of 1-methyl-2-pyrrolidinone was added dropwise and the mixture was stirred until ≦1.0% of the starting aniline remained (3-16 hours). The reaction was quenched with water and the mixture was warmed to 40° C. Aqueous sodium hydroxide (101 g in 750 ml) was added to bring the pH to 10-11. The resulting precipitates were filtered hot and washed with water. The wet solids were heated to reflux (70-75° C.) in acetonitrile:THF (1.5:1) and the solution was cooled over 3 hours to room temperature. The product was filtered and washed with acetonitrile:THF. The product was dried (50° C., 10 mm Hg, 24 h) and obtained in 80-85% yield. Melting Point 165-167° C.

EXAMPLE 4

4-Benzyloxy-3-chloro-nitrobenzene

A 15.43 g (0.275 moles) portion of solid (pellets) potassium hydroxide was added to a solution of 43.89 g (0.25 moles) of 3-chloro-4-fluoro nitrobenzene and 32.34 ml (33.79 grams, 0.373 moles) of benzyl alcohol in 220 ml of acetonitrile. The reaction was vigorously stirred with a mechanical stirrer overnight. The resulting solid was filtered. Concentration of the filtrate gave a second crop, which was also filtered. On standing more solid came out of this filtrate. This mixture was treated with ether, and the solid filtered. All solids were washed thoroughly with water, and combined to give 49.71 g of the title compound.

EXAMPLE 5

4-Benzyloxy-3-chloro-phenylamine

A mixture of 6.59 g (0.025 moles) of the 4-benzyloxy-3-chloro nitrobenzene (example 4), 4.19 g (0.075 moles) of iron powder, and 12.04 g (0.225 moles) of ammonium chloride in 100 ml of ethanol and 25 ml of water was stirred mechanically and refluxed for half an hour. The reaction was allowed to cool and stir for 1 hour. The mixture was filtered and solids were washed with ethanol. The combined filtrates were taken to dryness in vacuo. This solid was dissolved in methylene chloride and passed through Magnesol. Removal of the solvent from the filtrate in vacuo gave 5.60 g of title compound.

EXAMPLE 6

N-{4-[4-(Benzyloxy)-3-chloroanilino]-3-cyano-7-ethoxy-6-quinolinyl}acetamide A mixture of 4.17 g (0.0149 moles) of the N-(4-chloro-3-cyano-7-ethoxy-6-quinolinyl)acetamide, 4.04 g (0.0173 moles) of 4-benzyloxy-3-chloro-phenylamine (example 5), and 2.0 g (0.017 moles) of pyridine hydrochloride in 85 ml of isopropanol was stirred and refluxed in an oil bath for 30 minutes. The reaction was cooled in an ice bath, and the solid was collected by filtration and washed with isopropanol, and then with ether yielding 7.26 g of crude product as the hydrochloride salt. This material was purified by chromatography of the free base on silica gel by elution with 1:39 methanol-methylene chloride.

EXAMPLE 7

6-Amino-4-[4-(benzyloxy)-3-chloroanilino]-7-ethoxy-3-quinolinecarbonitrile

A solution of 298 mg (0.612 mmoles) of the purified N-{4-[4-(benzyloxy)-3-chloroanilino]-3-cyano-7-ethoxy-6-quinolinyl}acetamide (example 6) and 97 mg (1.73 mmoles) of potassium hydroxide in 10 ml of methanol was stirred and refluxed for 60 hours. On cooling a solid formed. This mixture was poured onto ice, and the resulting solid was filtered and washed with water. On drying, 242 mg of the title compound was obtained.

EXAMPLE 8

2-Acetamido-5-nitrophenol

To 400 g of 2-amino-5-nitrophenol in a 5-L multi-necked flask equipped with a mechanical stirrer, reflux condenser, nitrogen inlet, 500-mL addition funnel, heating mantle, and a thermocouple attached to a temperature controller was added 1.6 L of acetic acid. The mixture was stirred at 60° C. as 398 g of acetic anhydride was added over 1.5 hours. After 1 hour, another 37 g of acetic anhydride was added. After another 1 hour, the mixture was cooled and diluted with 2 L of water. Solid was collected by filtration and washed with water and heptane. The solid was dried in a vacuum oven to give 509 g of the title compound.

EXAMPLE 9

4-Acetamido-3-ethoxynitrobenzene

To 400 g of 2-acetamido-5-nitrophenol in a 12-L, 4-necked flask equipped with a reflux condenser, nitrogen inlet, thermocouple, addition funnel, and mechanical stirrer was added 790 g of potassium carbonate and 2.0 L of dimethylformamide. The mixture was stirred at 60° C. as 294 g of ethyl bromide was added over 30 minutes. After 1 hour, an additional 27 g of ethyl bromide was added and the mixture was stirred at 60° C. for another hour. The mixture was cooled to room temperature and poured into 4 L of water. After 30 minutes, the product was collected by filtration and washed with water and heptane. The product was dried in a vacuum oven at 60° C. to give 457 g of the title compound.

EXAMPLE 10

3-(4-Acetamido-3-ethoxyaniline)-2-cyanopropenoic acid ethyl ester

A suspension of 4-acetamido-3-ethoxynitrobenzene compound in tetrahydrofuran (10 parts) was reduced to the aniline derivative using 10% Pd/C wet at 50 psi hydrogen and 30° C. for 2 hours. The resulting solution was filtered and concentrated to 2 parts of tetrahydrofuran. The concentrate was diluted with toluene and allowed to react with commercially available ethyl (ethoxymethylene)cyanoacetate at reflux for 16 hours. After reaction completion, the mixture was cooled. The precipitated product was collected by filtration, washed and dried. The product was obtained in 90% yield.

EXAMPLE 11

3-Cyano-7-ethoxy-4-hydroxy-6-N-acetylquinoline

A solution of 210 g of 3-(4-acetamido-3-ethoxyaniline)-2-cyanopropenoic acid ethyl ester in 12 L of Dowtherm was stirred under nitrogen at 250° C. for 15 to 20 hours. The mixture was cooled to room temperature and solid was collected by filtration. The solid was washed with toluene and mixed with 1.2 L of tetrahydrofuran. The mixture was refluxed for 30 minutes and then cooled to room temperature. The solid was collected and washed with tetrahydrofuran. After drying 179.4 g of the title compound was obtained.

EXAMPLE 12

4-Chloro-3-cyano-7-ethoxy-6-nitro quinoline

A stirred mixture of 300 g 3-cyano-7-ethoxy-4-hydroxy-6-N-acetylquinoline in 2.53 L of 1,2-diethoxyethane was heated to 80-85° C. To this was added 224 ml of phosphorus oxychloride over 30-40 minutes. The mixture was stirred at 80-85° C. for 2-4 hours. The mixture was cooled, filtered over a celite pad and washed with 1,2-diethoxyethane. The filtrates were added over 1.5 hours to a cooled (0-10° C.) potassium carbonate (537 g in 1.5 L water) solution. The resulting yellow mixture was stirred for a minimum of 12 hours. The mixture was filtered and washed with hot water. The solids

EXAMPLE 13

3-Chloro-4-(2-pyridylmethoxy)nitrobenzene

A mixture of 160 g of potassium hydroxide and 2-pyridylcarbinol in 8 L acetonitrile was stirred for 20-30 minutes. To this was added 400 g of 3-chloro-4-fluoronitrobenzene and the mixture was stirred at 40° C. for a minimum of 18 hours until the reaction was complete. Water was added and the precipitated yellow solids were filtered and washed with water. The product was dried (40-50° C., 10 mm Hg, 24 h) to the product in 85-95% yield.

EXAMPLE 14

3-Chloro-4-(3-fluorobenzyloxy)nitrobenzene

This compound was prepared from 3-chloro-4-fluoronitrobenzene and 3-fluorobenzyl alcohol using the method described above in Example 13.

EXAMPLE 15

6-Amino-4-(3-chloro-4-(3-fluorobenzyloxy))anilino-3-cyano-7-ethoxy quinoline

To a mixture of 400 g of 3-chloro-4-(3-fluorobenzyloxy) nitrobenzene (example 14) and 464 g zinc dust in 4 L of ethanol at 40-50° C. was added aqueous ammonium chloride (152 g in 800 ml water). After stirring a minimum of 2 hours, the reaction mixture was filtered hot through a celite pad and washed with hot ethanol. The filtrate was evaporated and 1.72 L of 2-methyl THF, water and brine were added. The organic layer was separated and washed with water. The organic layer was evaporated and replaced with 3.8 L of ethanol. 4-Chloro-3-cyano-7-ethoxy-6-N-acetylamino-quinoline was added with a catalytic amount of methane sulfonic acid and the mixture was heated at 70-75° C. for a minimum of 2 hours until reaction completion. Concentrated 1.69 L HCl was added at 70-75° C. and held for a minimum of 2 hours until complete hydrolysis. Water was added and the mixture was cooled to 40° C., solid was collected and washed with water. The wet cake was slurried in 5.4 L of methanol, 10% aqueous potassium carbonate (315 g in 2.8 L water) was added and the mixture was stirred for 2.5 hours. The mixture was filtered and washed with 1:1 methanol:water. The product was dried (50° C., 10 mm Hg, 24 hours) to give the title compound in 80-90% yield.

EXAMPLE 16

6-Amino-4-(4-(2-pyridylmethoxy)-3-chloro)anilino-3-cyano-7-ethoxyquinoline

The above-identified compound was prepared from 3-chloro-4-(2-pyridylmethoxy)nitrobenzene and 4-chloro-3-cyano-7-ethoxy-6-N-acetylamino-quinoline using the method described above in Example 15.

EXAMPLE 20

4-Dimethyl-but-2-enoic acid [4-(3-chloro-4-fluoro-phenylamino)-3-cyano-7-ethoxy-quinolin-6-yl]-amide were dried (50° C., 10 mm Hg, 24 h) to give the title compound in 30-50% yield. The material was used directly in the next step.

EXAMPLE 21

N-{4-[3-Chloro-4-(1-methyl-1H-imidazol-2-ylsulfanyl)-phenylamino]-3-cyano-quinolin-6-yl}-acrylamide

EXAMPLE 22

6,7-Diethoxy-4-(1H-indol-6-ylamino)-quinoline-3-carbonitrile

EXAMPLE 23

4-(2,3-Dihydro-benzo[1,4]dioxin-6-ylamino)-6,7-diethoxy-quinoline-3-carbonitrile

EXAMPLE 24

4-(1H-Indazol-6-ylamino)-6,7-bis-(2-methoxy-ethoxy)-quinoline-3-carbonitrile

EXAMPLE 25

4-(1,4-Dioxo-1,2,3,4-tetrahydro-phthalazin-6-ylamino)-6,7-diethoxy-quinoline-3-carbonitrile

EXAMPLE 26

6,7-Diethoxy-4-(indan-5-ylamino)-quinoline-3-carbonitrile

EXAMPLE 27

4-(2,4-Dioxo-1,4-dihydro-2H-benzo[d][1,3]oxazin-6-ylamino)-6,7-diethoxy-quinoline-3-carbonitrile

EXAMPLE 28

6,7-Diethoxy-4-(1-oxo-indan-5-ylamino)-quinoline-3-carbonitrile

EXAMPLE 29

6,7-Diethoxy-4-(3-oxo-1,3-dihydro-isobenzofuran-5-ylamino)-quinoline-3-carbonitrile

EXAMPLE 30

4-(1,1-Dioxo-1H-1-benzo[b]thiophen-6-ylamino)-6,7-diethoxy-quinoline-3-carbonitrile

EXAMPLE 31

7-Ethoxy-4-(1H-indazol-6-ylamino)-6-methoxy-quinoline-3-carbonitrile

EXAMPLE 32

6-Ethoxy-4-(1H-indazol-6-ylamino)-7-methoxy-quinoline-3-carbonitrile

EXAMPLE 33

6,7-Diethoxy-4-(1-methyl-2,5-dioxo-2,3,4,5-tetrahydro-1H-benzo[e][1,4]diazepin-7-ylamino)-quinoline-3-carbonitrile

EXAMPLE 34

4-(1H-Indazol-6-ylamino)-6-methoxy-7-(3-morpholin-4-yl-propoxy)-quinoline-3-carbonitrile

EXAMPLE 35

4-({3-chloro-4-[(1-methyl-1H-imidazol-2-yl)sulfanyl]phenyl}amino)-7-methoxy-6-nitro-3-quinolinecarbonitrile

EXAMPLE 36

6-amino-4-({3-chloro-4-[(1-methyl-1H-imidazol-2-yl)sulfanyl]phenyl}amino)-7-methoxy-3-quinolinecarbonitrile

EXAMPLE 37

(2E)-N-[4-({3-chloro-4-[(1-methyl-1H-imidazol-2-yl)sulfanyl]phenyl}amino)-3-cyano-7-methoxy-6-quinolinyl]-4-(dimethylamino)-2-butenamide

EXAMPLE 38

4-{[3-chloro-4-(1,3-thiazol-2-ylsulfanyl)phenyl]amino}-7-methoxy-6-nitro-3-quinolinecarbonitrile

EXAMPLE 39

6-amino-4-{[3-chloro-4-(1,3-thiazol-2-ylsulfanyl)phenyl]amino}-7-methoxy-3-quinolinecarbonitrile

EXAMPLE 40

(2E)-N-(4-{[3-chloro-4-(1,3-thiazol-2-ylsulfanyl)phenyl]amino}-3-cyano-7-methoxy-6-quinolinyl)-4-(dimethylamino)-2-butenamide

EXAMPLE 41

4-[3-chloro-4-(1H-imidazol-1-yl)anilino]-7-methoxy-6-nitro-3-idazol-1-yl)anilino ]-7-methoxy-6-nitro-3-quinolinecarbonitrile

EXAMPLE 42

6-amino-4-[3-chloro-4-(1H-imidazol-1-yl)anilino]-7-methoxy-3-4-(1H-imidazol -1-yl)anilino]-7-methoxy-3-quinolinecarbonitrile

EXAMPLE 43

(E)-N-{4-[3-chloro-4-(1H-imidazol-1-yl)anilino]-3-cyano-7-methoxy-6-quinolinyl}-azol-1-yl)anilino]-4-(dimethylamino)-2-)anilino-2-butenamide

EXAMPLE 44

4-{3-chloro-4-[(4-oxo-3,4-dihydro-2-quinazolinyl)sulfanyl]anilino}-7-methoxy-6-hydro-2-quinazolinyl)sulfanyl]anilino}-7-methoxy-6-nitro-3-quinolinecarbonitrile

EXAMPLE 45

6-amino-4-{3-chloro-4-[(4-oxo-3,4-dihydro-2-quinazolinyl)sulfanyl]anilino}-7-3,4-dihydro-2-quinazolinyl)sulfanyl]anilino}-7-methoxy-3-quinolinecarbonitrile

EXAMPLE 46

(E)-N-(4-{3-chloro-4-[(4-oxo-3,4-dihydro-2-quinazolinyl)sulfanyl]anilino}-3-fanyl]anilino}-3-cyano-7-methoxy-6-quinolinyl)-4-(dimethylamino)-2-butenamide

EXAMPLE 47

(E)-N-(4-{4-[acetyl(3-pyridinylmethyl)amino]-3-chloroanilino≠-3-cyano-7-methoxy-]-3-chloroanilino}-3-cyano-7-methoxy-]-3-chloroanilino}-3-cyano-7-methoxy-6-quinolinyl)-4-(dimethylamino)-2-oanilino}-3-cyano-7-methoxy-6-quinolinyl)-4-(dimethylamino)-2-butenamide

EXAMPLE 48

N-{2-chloro-4-[(3-cyano-7-methoxy-6-nitro-4-quinolinyl)amino]phenyl}-N-(3-7-methoxy-6-nitro-4-quinolinyl)amino]phenyl}-N-(3-pyridinylmethyl)acetamide

EXAMPLE 49

N-{4-[(6-amino-3-cyano-7-methoxy-4-quinolinyl)amino]-2-chlorophenyl}-N-(3—methoxy-4-quinolinyl)amino]-2-chlorophenyl}-N-(3-pyridinylmethyl)acetamide

EXAMPLE 50

N-(4-{[6-(acetylamino)-3-cyano-7-methoxy-4-quinolinyl]amino]-2-chlorophenyl)-N-ano-7-methoxy-4-quinolinyl]amino]-2-chlorophenyl)-N-(3-pyridinylmethyl)acetamide

EXAMPLE 51

4-{3-chloro-4-[(1-methyl-1H-imidazol-2-yl)sulfanyl]anilino}-6-methoxy-7-[3-4-morpholinyl)propoxy]-3-quinolinecarbonitrite

EXAMPLE 52

4-(3-chloro-4-{[5-(trifluoromethyl)-1,3,4-thiadiazol-2-yl]amino}anilino)-7-ethoxy-6 -nitro-3-quinolinecarbonitrile

EXAMPLE 53

(E)-N-[4-(3-chloro-4-{[5-(trifluoromethyl)-1,3,4-thiadiazol-2-yl]amino}anilino)-3-cyano-7-ethoxy-6-quinolinyl]-4-(dimethylamino)-2-butenamide

EXAMPLE 54

4-[3-chloro-4-(4-pyridinyloxy)anilino]-7-ethoxy-6-nitro-3-quinolinecarbonitrile

EXAMPLE 55

6-amino-4-[3-chloro-4-(4-pyridinyloxy)anilino]-7-ethoxy-3-quinolinecarbonitrile

EXAMPLE 56

(E)-N-{4-[3-chloro-4-(4-pyridinyloxy)anilino]-3-cyano-7-ethoxy-6-quinolinyl}-4-(dimethylamino)-2-butenamide

EXAMPLE 57

4-{3-chloro-4-[(3-pyridinylmethyl)amino]anilino}-7-methoxy-6-nitro-3-quinolinecarbonitrile

EXAMPLE 58

(E)-N-(4-{3-chloro-4-[(4-phenyl-1,3-thiazol-2-yl)sulfanyl]anilino}-3-cyano-7-methoxy-6-quinolinyl)-4-(dimethylamino)-2-butenamide

EXAMPLE 59

6-amino-4-(3-chloro-4-{[5-(trifluoromethyl)-1,3,4-thiadiazol-2-yl]amino}anilino)-7-ethoxy-3-quinolinecarbonitrile

EXAMPLE 60

4-[3-chloro-4-(1H-imidazol-1-ylmethyl)anilino]-7-ethoxy-6-nitro-3-quinolinecarbonitrile

EXAMPLE 61

6-amino-4-[3-chloro-4-(1H-imidazol-1-ylmethyl)anilino]-7-ethoxy-3-quinolinecarbonitrile

EXAMPLE 62

(E)-N-{4-[3-chloro-4-(1H-imidazol-1-ylmethyl)anilino]-3-cyano-7-ethoxy-6-quinolinyl}-4-(dimethylamino)-2-butenamide

EXAMPLE 63

4-{3-chloro-4-[(4-methyl-2-pyrimidinyl)sulfanyl]anilino}-7-ethoxy-6-nitro-3-quinolinecarbonitrile

EXAMPLE 64

6-amino-4-{3-chloro-4-[(4-methyl-2-pyrimidinyl)sulfanyl]anilino}-7-ethoxy-3-quinolinecarbonitrile

EXAMPLE 65

(E)-N-(4-{3-chloro-4-[(4-methyl-2-pyrimidinyl)sulfanyl]anilino}-3-cyano-7-ethoxy-6-quinolinyl)-4-(dimethylamino)-2-butenamide

EXAMPLE 66

(E)-N-(4-{3-chloro-4-[(4,6-dimethyl-2-pyrimidinyl)sulfanyl]anilino}-3-cyano-7-ethoxy-6-quinolinyl)-4-(dimethylamino)-2-butenamide

EXAMPLE 67

7-ethoxy-6-nitro-4-[4-[(4-phenyl-1,3-thiazol-2-yl)sulfanyl]-3-(trifluoromethyl) anilino]-3-quinolinecarbonitrile

EXAMPLE 68

6-Amino-7-ethoxy-4-[4-(4-phenyl-thiazol-2-ylsulfanyl)-3-trifluoromethyl-phenylamino]-quinoline-3-carbonitrile

EXAMPLE 69

(E)-N-{3-cyano-7-ethoxy-4-[4-[(4-phenyl-1,3-thiazol-2-yl)sulfanyl]-3-(trifluoromethyl)anilino]-6-quinolinyl}-4-(dimethylamino)-2-butenamide

EXAMPLE 70

(E)-N-(4-{3-chloro-4-[(5-phenyl-1,3-thiazol-2-yl)sulfanyl]anilino}-3-cyano-7-methoxy-6-quinolinyl)-4-(dimethylamino)-2-butenamide

EXAMPLE 71

(E)-N-{4-[3-chloro-4-(1,3-thiazol-2-ylsulfanyl)anilino]-3-cyano-7-methoxy-6-quinolinyl}-4-[(2-methoxyethyl)(methyl)amino]-2-butenamide (E)-N-{4-[3-chloro-4-(1,3-thiazol-2-ylsulfanyl)anilino]-3-cyano-7-methoxy-6-quinolinyl}-4-[(2-methoxyethyl)(methyl)amino]-2-butenamide was prepared by adding dropwise, 3.43 g (18.71 mmol, 1.95 mL) 4-bromocrotonyl chloride in 12 mL THF over 45 minutes to a stirred solution of 4.7 g (10.69 mmol) 6-amino-4-[3-chloro-4-(thiazol-2-ylsulfanyl)-phenylamino]-7-methoxy-quinolin-3-carbonitrile in 588 mL THF containing 3.73 mL (21.36 mmol) diisopropylethylamine, at 0° C. under nitrogen. The reaction produced a mixture of 4-bromo-(and chloro)-but-2-enoic acid {4-[3-chloro-4-(thiazol-2-ylsulfanyl)-phenylamino]-3-cyano-7-methoxy-quinolin-6-yl}-amide. A 300 mL portion of the solution was cooled to 0° C. and 2.38 g (26.7 mmol) (2-methoxyethyl)-methylamine in 11 mL THF was added dropwise. After the reaction had warmed to room temperature, 401 mg (0.5 eq) of sodium iodide was added and the solution was stirred overnight. The solvents were evaporated to leave a red gum, which was partitioned between EtOAc and saturated NaHCO$_3$. After standing overnight, the layers were separated and the organic layer was dried and evaporated. Chromatography of the residue on a short column of Kieselgel 60, eluting with EtOAc, then EtOAc/15% MeOH, and finally EtOAc/15% MeOH/1% Et$_3$N yielded 1.3 g (41%) of the product as a yellow glass; HRMS (ESI) m/z 595.13338 (M)$^{+1}$, Δ=−2.28 mmu.

EXAMPLE 72

(E)-N-(4-{3-chloro-4-[(4-phenyl-1,3-thiazol-2-yl)sulfanyl]anilino}-3-cyano-7-ethoxy-6-quinolinyl)-4-(dimethylamino)-2-butenamide

EXAMPLE 73

4-{3-chloro-4-[(1-methyl-1H-imidazol-2-yl)sulfanyl]anilino}-6-methoxy-7-[3-triazol-1-yl)propoxy]-3-quinolinecarbonitrile

EXAMPLE 74

4-{3-chloro-4-[(4,6-dimethyl-2-pyrimidinyl)sulfanyl]anilino}-7-ethoxy-6-nitro-3-quinolinecarbonitrile

EXAMPLE 75

6-amino-4-{3-chloro-4-[(4,6-dimethyl-2-pyrimidinyl)sulfanyl]anilino}-7-ethoxy-3-quinolinecarbonitrile

EXAMPLE 76

(2E)-N-{4-[3-chloro-4-(2-thienylmethoxy)anilino]-3-cyano-7-ethoxy-6-quinolinyl}-4-(dimethylamino)-2-butenamide Representative compounds of this invention were evaluated in several standard pharmacological test procedures that showed that the compounds of this invention possess significant activity as inhibitors of HER-2 and are antiproliferative agents. Based on the activity shown in the standard pharmacological test procedures, the compounds of this invention are therefore useful as antineoplastic agents. The test procedures used and results obtained are shown below.

Kinase Assays: example 1, example 2 and example 3 are potent inhibitors of the HER-2 enzyme, example 20 is not. Purified recombinant C-terminal fragment of each enzyme is incubated with ATP in the absence or presence of a range of compound concentrations. Autophosphorylation of the receptors was evaluated with phosphotyrosine antibodies in an ELISA format. In a cell-free autophosphorylation assay using the recombinant cytoplasmic domain of HER-2, all three inhibitors reduced enzyme activity by 50% ($IC_{50}$) at concentrations between 33-65 nM (Table 1).

TABLE 1

| Compound | Enzyme $IC_{50}$ (µg/mL) | |
|---|---|---|
| | HER-2 | EGFR |
| Example 1 | 0.036 | 0.028 |
| Example 2 | 0.033 | 0.051 |
| Example 3 | 0.019 | 0.019 |
| Example 20 | 0.58 | 0.02 |

They also inhibited EGFR under similar assay conditions at 33-92 nM.

Cell Proliferation Assays: example 1, example 2, and example 3 repressed the proliferation of a mouse fibroblast cell line transfected with the HER-2 oncogene (3T31neu) by 50% ($IC_{50}$) at 3-5 nM (Table 2). This value was substantially lower than that obtained with the isogenic untransfected cells (3T3; $IC_{50}$ 683-906 nM), indicating a high degree of selectivity for this oncogenic pathway. Cells were incubated with various concentrations of compound for 2 days (6 days for BT474 cells). Cell survival was determined using a protein binding dye assay (SRB),(Rubinstein LV, Shoemaker R H, Paull K D, Simon R M, Tosini S, Skehan P, Scudiero D A, Monks A, Boyd M R. Comparison of in vitro anticancer-drug-screening data generated with a tetrazolium assay versus a protein assay against a diverse panel of human tumor cell lines. J. Natl. Cancer Inst. 82(13):1113-8, 1990, Skehan P, Storeng R, Scudiero D, Monks A, McMahon J, Vistica D, Warren JT, Bokesch H, Kenney S, Boyd MR. New colorimetric cytotoxicity assay for anticancer-drug screening. J. Natl. Cancer Inst. 82(13):1107-12, 1990).

The concentration of drug (nM) which inhibits enzyme activity or cell proliferation by 50% is shown. The three inhibitors also inhibited two other HER-2 overexpressing breast cancer cell lines, SK-Br-3 and BT474 ($IC_{50}$ 2-4 nM), but were much less active on MDA-MB-435 and SW620 cells (a breast cancer and a colon cancer cell line, respectively), that are EGFR— and HER-2-negative. The compounds repressed the epidermal carcinoma cell line, A431, that overexpresses EGFR ($IC_{50}$ 81-120 nM) (Table 2).

TABLE 2

| | CELL $IC_{50}$ (µg/mL) | | | | | | |
|---|---|---|---|---|---|---|---|
| EGFR | − | − | +++ | − | + | − | − |
| Her-2 | − | +++ | + | +++ | +++ | − | − |
| COMPOUND | 3T3 | 3T3/NEU | A431 | SKBr3 | BT474 | MDA-MB-435 | SW620 |
| Example 1 | 0.38 | 0.0029 | 0.062 | 0.0015 | 0.0014 | 0.47 | 0.24 |
| Example 2 | 0.39 | 0.0018 | 0.045 | 0.001 | 0.0013 | 0.44 | 0.44 |
| Example 3 | 0.52 | 0.0023 | 0.069 | 0.0015 | 0.0024 | 0.51 | 0.29 |
| Example 20 | 0.26 | 0.0230 | 0.030 | 0.0071 | 0.020 | 0.34 | 0.32 |
| Example 21 | | 0.463 | 0.62 | 0.01 | | 4.57 | 1.84 |
| Example 22 | | 0.933 | 0.123 | 0.0374 | | 0.365 | 0.286 |
| Example 23 | | 0.375 | 0.27 | 0.281 | | 0.235 | 0.411 |
| Example 24 | | >5 | 1.961 | >5 | | 2.045 | >5 |
| Example 25 | | >5 | >5 | >5 | | >5 | >5 |
| Example 26 | | 0.0198 | 0.342 | 0.294 | | 0.352 | 0.294 |

TABLE 2-continued

| | CELL IC$_{50}$ (µg/mL) | | | | | | |
|---|---|---|---|---|---|---|---|
| EGFR | − | − | +++ | − | + | − | − |
| Her-2 | − | +++ | + | +++ | +++ | − | − |
| COMPOUND | 3T3 | 3T3/NEU | A431 | SKBr3 | BT474 | MDA-MB-435 | SW620 |
| Example 27 | | 4.616 | >5 | >5 | | >5 | 2.922 |
| Example 28 | | 0.0311 | 0.0181 | 0.0281 | | 0.028 | 0.0244 |
| Example 29 | | 3.301 | >5 | >5 | | 3.404 | 1.565 |
| Example 30 | | 0.251 | 0.257 | 0.336 | | 0.00328 | 0.146 |
| Example 31 | | 0.0267 | 0.0368 | 0.022 | | 0.0359 | 0.0212 |
| Example 32 | | 4.801 | 0.786 | 2.094 | | 2.626 | 4.313 |
| Example 33 | | >5 | >5 | >5 | | >5 | >5 |
| Example 34 | | >5 | >5 | >5 | | >5 | >5 |
| Example 35 | | 4.09 | 2.88 | 0.669 | | 1 | 1.55 |
| Example 36 | | 1.06 | 3.04 | 0.011 | | 0.39 | 3.16 |
| Example 37 | | 0.02 | 0.02 | 0.0004 | | 0.43 | 0.43 |
| Example 38 | | 0.262 | 0.148 | 0.124 | | 0.35 | 0.15 |
| Example 39 | | 0.333 | 0.663 | 0.236 | | 0.65 | 0.55 |
| Example 40 | | 0.002 | 0.017 | 0.0007 | | 0.33 | 1.13 |
| Example 41 | | 1.09 | 1.79 | 1.48 | | 0.95 | 1.66 |
| Example 42 | | 0.53 | 1.63 | 1.73 | | 1.27 | 5.99 |
| Example 43 | | 1.46 | 0.51 | 0.32 | | 0.57 | 1.45 |
| Example 44 | | 4.54 | 2.28 | 4.54 | | >5 | 1.96 |
| Example 45 | | 1.88 | 1.22 | 2.15 | | 4.58 | 4.66 |
| Example 46 | | 0.15 | 0.34 | 0.06 | | >5 | >5 |
| Example 47 | | >5 | 0.646 | >5 | | 1.16 | 1.64 |
| Example 48 | | 1.79 | 1.6 | 0.68 | | 2.61 | 2.57 |
| Example 49 | | 2.4 | >5 | 3.41 | | 3.76 | >5 |
| Example 50 | | >5 | 3.68 | 3.94 | | >5 | >5 |
| Example 51 | | 0.196 | 0.775 | 0.32 | | | 2.18 |
| Example 52 | | 1.89 | 1.79 | 1.22 | | 1.84 | 2.54 |
| Example 53 | | 0.89 | 0.728 | 0.179 | | 0.95 | 1.05 |
| Example 54 | | >5 | >5 | >5 | | 2.54 | >5 |
| Example 55 | | >5 | >5 | >5 | | 1.61 | >5 |
| Example 56 | | >5 | 3.27 | 1.51 | | 2.06 | >5 |
| Example 57 | | 4.03 | 1.6 | 0.726 | | 1.87 | 3.21 |
| Example 58 | | 0.028 | 0.162 | 0.005 | | 0.23 | 0.57 |
| Example 59 | | >5 | >5 | 0.551 | | 0.91 | 1.38 |
| Example 60 | | >5 | >5 | 2.44 | | >5 | >5 |
| Example 61 | | >5 | >5 | 0.75 | | >5 | >5 |
| Example 62 | | 0.99 | 0.95 | 0.045 | | 2.1 | 3.8 |
| Example 63 | | 1.49 | 1.2 | 0.45 | | 1.3 | 0.9 |
| Example 64 | | 3.03 | 1.53 | >5 | | 1.8 | 2 |
| Example 65 | | 0.003 | 0.12 | 0.001 | | 0.3 | 0.2 |
| Example 66 | | 0.01 | 0.24 | 0.006 | | 0.2 | 0.32 |
| Example 67 | | 0.68 | 0.76 | 0.268 | | 0.4 | 0.4 |
| Example 68 | | 2.52 | >5 | 0.943 | | 2.5 | 3.1 |
| Example 69 | | 0.42 | 0.3 | >5 | | 0.3 | 0.6 |
| Example 70 | | 0.12 | 0.22 | 0.01 | | 0.08 | 0.5 |
| Example 71 | | 0.002 | 0.03 | 0.002 | | 0.09 | 0.4 |
| Example 72 | | 0.02 | 0.24 | 0.006 | | 0.18 | 0.54 |
| Example 73 | | 0.973 | 1.83 | 0.104 | | | 3.69 |
| Example 74 | | >5 | >5 | >5 | | 4.1 | >5 |
| Example 75 | | 2.12 | 0.76 | 0.98 | | 1.3 | 1.36 |
| Example 76 | 0.41 | 0.0039 | 0.066 | 0.004 | 0.003 | 0.77 | 0.25 |

Receptor Phosphorylation: Compounds that repressed the proliferation of a mouse fibroblast cell line transfected with the HER-2 oncogene (3T3/neu) by 50% (IC$_{50}$) <0.05 µg/ml in Table 2 above were tested for in vitro phosphorylation. For Her-2 and EGFR phosphorylation assays, cells (BT474 and A431, respectively) were incubated with various concentrations of compound for 3 hours at 37° C. Protein extracts were analyzed by immunoblotting using phospho-tyrosine antibodies. Blots were quantified by densitometric scanning. Concentration of compound (nM) which inhibits phosphorylation by 50% was determined. Example 1, Example 3 and HKI-272 decreased ligand-independent receptor phosphorylation by 50% (IC$_{50}$) at 5-23 nM in BT474 cells (Table 3). They also repressed EGF-dependent phosphorylation of EGFR in A431 cells at a comparable dose (IC$_{50}$ 3-7 nM).

TABLE 3

| | IC50 (µg/mL) | |
|---|---|---|
| Compound | BT474 | A431 |
| Example 1 | 0.0075 | 0.0031 |
| Example 2 | 0.0026 | 0.0014 |

TABLE 3-continued

| | IC50 (µg/mL) | |
|---|---|---|
| Compound | BT474 | A431 |
| Example 3 | 0.013 | 0.0042 |
| Example 20 | 0.080 | 0.0031 |
| Example 37 | <1 | |
| Example 40 | 10-50 | |
| Example 58 | 50-500 | |
| Example 76 | 0.0015 | 0.0025 |

IN VIVO: The in vivo antitumor activity of example 3 was evaluated in tumor xenograft models. Tumor cells (grown in tissue culture) or tumor fragments were implanted subcutaneously in female nude mice. Treatment was initiated after tumors had reached a size of 90-200 mg, following random assignment of the animals to different treatment groups (staging). Alternatively (3T3/neu), treatment was initiated the day after tumor implantation, due to the rapid outgrowth of these tumors. Compounds were formulated in 0.5% Methocel-0.4% polysorbate-80 (Tween-80) and administered daily, PO, by gavage. Tumor mass $[(L \times W^2)/2]$ was determined every 7 days. Statistical significance of compound effects was evaluated using Student's t-test.

The activity of example 3 was first evaluated in xenografts of 3T3/neu cells example 3 inhibited tumor growth when administered to animals at 20 mg/kg/day (65% inhibition, day 21), 40 mg/kg/day (97% inhibition), and 80 mg/kg/day (99% inhibition). These results were almost identical to those obtained with example 2 treatment (53%, 95%, and 98% inhibition, respectively at 20, 40 and 80 mg/kg/day). In two other independent tests, EXAMPLE 3 treatment produced a statistically-significant inhibition of tumor growth (21-33%) at a dose of 10 mg/kg/day. Based on these studies, the minimum efficacious dose (MED) was estimated to be 10 mg/kg/day. This is the smallest dose that produces a sustained, statistically-significant ($p<0.05$) reduction of tumor growth.

The effect of example 3 was next studied in xenografts of HER-2-dependent human tumor cell lines. In animals bearing BT474 xenografts, example 3 treatment reduced tumor growth when dosed between 10 mg/kg/day and 40 mg/kg/day. Maximum inhibition was observed on day 21, and ranged from 59% (10/mg/kg/day) to 96% (40 mg/kg/day). For example 2, inhibition ranged from 76% (10 mg/kg/day) to 95% (40 mg/kg/day). Similar results were obtained in two other independent experiments. In animals bearing xenografts of SUM-190 (a second HER-2-dependent breast cancer cell line), example 3 treatment resulted in substantial repression of tumor growth when dosed at 40 mg/kg/day (94% inhibition, day 28). Example 3 was also effective against xenografts of SK-OV-3 (a HER-2-dependent human ovarian carcinoma cell line). Here, example 3 was active between 20 mg/kg/day (86% inhibition, day 35) and 60 mg/kg/day (91% inhibition). The MED in the HER-2 over-expressing human xenograft models was estimated at 10 mg/kg/day, similar to example 2. In these studies, there was no decrease in tumor size below the initial size at the start of dosing. Furthermore, tumors showed evidence of re-growth when treatment was completed, which is consistent with a non-cytotoxic mode of action for example 3.

What is claimed is:

1. A compound:
   (E)-N-{4-[4-(benzyloxy)-3-chloroanilino]-3-cyano-7-ethoxy-6-quinolinyl}-4-(dimethylamino)-2-butenamide or a pharmaceutically acceptable salt thereof.

2. A compound: (E)-N-{4-[3-chloro-4-(2-pyridinylmethoxy)anilino]-3-cyano-7-ethoxy-6-quinolinyl}-4-(dimethylamino)-2-butenamide or a pharmaceutically acceptable salt thereof.

3. A compound: (E)-N-(4-{3-chloro-4-[(3-fluorobenzyl)oxy]anilino}-3-cyano-7-ethoxy-6-quinolinyl)-4-(dimethylamino)-2-butenamide or a pharmaceutically acceptable salt thereof.

4. A compound: (2E)-N-(4-{[3-chloro-4-(1,3-thiazol-2-ylsulfanyl)phenyl]amino}-3-cyano-7-methoxy-6-quinolinyl)-4-(dimethylamino)-2-butenamide or A compound: (E)-N-(4-{3-chloro-4-[(4,6-di-methyl-2-pyrimidinyl)sulfanyl]anilino}-3-cyano-7-ethoxy-6-quinolinyl)-4-(dimethylamino)-2-butenamide or a pharmaceutically acceptable salt thereof.

5. A compound (E)-N-{4-[3-chloro -4-(1,3-thiazol-2-ylsulfanyl )anilino]-3-cyano-7-methoxy-6-quinolinyl}-4-[(2-methoxyethyl)(methyl)amino]-2-butenamide or a pharmaceutically acceptable salt thereof.

6. A pharmaceutical composition comprising: (E)-N-{4-[4-(benzyloxy)-3-chloroanilino]-3-cyano-7-ethoxy-6-quinolinyl}-4-(dimethylamino)-2-butenamide or a pharmaceutically acceptable salt thereof, and a pharmaceutically acceptable carrier.

7. A pharmaceutical composition comprising: (E)-N-{4-[3-chloro-4-(2-pyridinylmethoxy)anilino]-3-cyano-7-ethoxy-6-quinolinyl}-4-(dimethylamino)-2-butenamide or a pharmaceutically acceptable salt thereof, and a pharmaceutically acceptable carrier.

8. A pharmaceutical composition comprising: (E) -N-(4-{3-chloro-4-[(3-fluorobenzyl)oxy]anilino}-3-cyano-7-ethoxy-6-quinolinyl)-4-(dimethylamino)-2-butenamide or a pharmaceutically acceptable salt thereof, and a pharmaceutically acceptable carrier.

9. A pharmaceutical composition comprising: (E)-N-(4-{3-chloro-4-[(4-methyl-2-pyrimidinyl)sulfanyl]anilino}-3-cyano -7-ethoxy-6-quinolinyl)-4-(dimethylamino)-2-butenamide or a pharmaceutically acceptable salt thereof, and a pharmaceutically acceptable carrier.

10. A pharmaceutical composition comprising (E)-N-{4-[3-chloro-4-(1,3-thiazol-2-ylsulfanyl )anilino]-3-cyano-7-methoxy-6-quinolinyl}-4-[(2-methoxyethyl)(methyl)amino]-2-butenamide or a pharmaceutically acceptable salt thereof, and a pharmaceutically acceptable carrier.

* * * * *

UNITED STATES PATENT AND TRADEMARK OFFICE

(12)             CERTIFICATE EXTENDING PATENT TERM
UNDER 35 U.S.C. 156

| | | | |
|---|---|---|---|
| (68) | PATENT NO. | : | 7,399,865 |
| (45) | ISSUED | : | July 15, 2008 |
| (75) | INVENTOR | : | Allan Wissner et al. |
| (73) | PATENT OWNER | : | Wyeth LLC |
| (95) | PRODUCT | : | NERLYNX® (neratinib) |

This is to certify that an application under 35 U.S.C. 156 has been filed in the United States Patent and Trademark Office, requesting extension of the term of U.S. Patent No. 7,399,865 based upon the regulatory review of the product NERLYNX® (neratinib) by the Food and Drug Administration. According to United States Patent and Trademark Office records, the original expiration date of the patent as of the date of issuance of this certificate is December 29, 2025. Because it appears that the requirements of the law have been met, this certificate extends the term of the patent for the period of

(94)                                5 years subject to the payment of maintenance fees as provided by law, with all rights pertaining thereto as provided by 35 U.S.C. 156.

I have caused the seal of the United States Patent and Trademark Office to be affixed this 19th day of November 2021.

Andrew Hirshfeld
Commissioner for Patents, Performing the Functions and Duties of the Under Secretary of Commerce for Intellectual Property and Director of the United States Patent and Trademark Office